(12) United States Patent
Tomilson et al.

(10) Patent No.: US 7,761,149 B2
(45) Date of Patent: Jul. 20, 2010

(54) ELECTRICAL STIMULUS ALLERGY TREATMENT METHOD

(75) Inventors: Andrew Robert Tomilson, Oakville (CA); Silvana Fazzolari, Oakville (CA); John Stewart, Oakville (CA)

(73) Assignee: The Institute of Natural Health Technologies, Inc., Ontario (CA)

( * ) Notice: Subject to any disclaimer, the term of this patent is extended or adjusted under 35 U.S.C. 154(b) by 569 days.

(21) Appl. No.: 11/728,992

(22) Filed: Mar. 28, 2007

(65) Prior Publication Data

US 2008/0243199 A1    Oct. 2, 2008

(51) Int. Cl.
*A61N 1/32*    (2006.01)
(52) U.S. Cl. ............................................. 607/3; 604/20
(58) Field of Classification Search ................. 607/3; 604/20; 128/907
See application file for complete search history.

(56) References Cited

U.S. PATENT DOCUMENTS

| | | | |
|---|---|---|---|
| 6,125,301 A * | 9/2000 | Capel | 607/74 |
| 6,142,927 A | 11/2000 | Clark | |
| 7,217,281 B2 * | 5/2007 | Bernstein | 607/89 |
| 2004/0098036 A1 | 5/2004 | Bergersen | |
| 2004/0230256 A1 * | 11/2004 | Lin-Hendel | 607/72 |
| 2005/0101031 A1 | 5/2005 | Hiller et al. | |
| 2005/0203578 A1 * | 9/2005 | Weiner et al. | 607/2 |

OTHER PUBLICATIONS

Semizzi et al. "A double-blind, placebo-controlled study on the diagnostic accuracy of an electrodermal test in allergic subjects" Clinical and Experimental Allergy, 2002. 32:928-932.*
Galitzer, Michael "Clinical Bioenergetics International Academy of Modern Bioenergetics" 1994.*
International Search Report mailed Nov. 21, 2008 for corresponding PCT/IB08/00732.

* cited by examiner

*Primary Examiner*—Carl H Layno
*Assistant Examiner*—Yun Haeng Lee
(74) *Attorney, Agent, or Firm*—Harris Beach LLP; Neal L. Slifkin

(57) ABSTRACT

A method of reducing the symptoms of allergy including exposing the patient to the allergenic substance in containers and applying an electrical stimulus device to acupuncture meridian points on the patient's body to clear blockages in the flow of life-energy of the patient. The electrical signal acts as a carrier for the natural frequency of the allergen, exposing the patient to the natural frequency of the allergen, carried by the electrical signal.

14 Claims, 5 Drawing Sheets

ELECTRICAL STIMULUS ALLERGY TREATMENT METHOD

FIELD OF THE INVENTION

This invention relates to methods for reducing the symptoms of allergic reactions using electrical energy stimulation. More particularly, this invention relates to applying low amperage, pulsed electrical energy having a controlled frequency to acupuncture meridians to reduce the symptoms of allergies.

BACKGROUND OF THE INVENTION

Some ancient, traditional, and present Eastern health and medical practices involve the concept and theory of an invisible life-energy that permeates the environment, and circulates in the human body via a system of channels and gateways. This invisible life-energy is called "qi" or "chi". Certain Eastern medical treatments involve delivering and improving the flow of this life-energy to the ill. One such example is acupuncture, which uses acupuncture needles punctured through a patient's skin to gateways to his or her life-energy channels to derive energy from the environment to unblock the patient's blockage in his life-energy flow.

Traditional Chinese acupuncture is widely practiced all over the world for enhancing health and treating illnesses. To practice acupuncture, the practitioner inserts small gauge needles through skin, ranging from approximately 2 mm to 2.5 cm deep, into specific sets of points in a system of meridians. The acupuncture treatment is based on twelve meridians on each side of the body and two master meridians along the center line of the body. These meridians are channels where life-energy circulates. Each meridian contains from about twenty-five to about one-hundred fifty acupuncture points. The points where the acupuncture needles are inserted are the specific sites located in the superficial cutaneous layer generally beneath the surface skin, and above the muscle regions, through which the life-energy is gated to the body surface. External energy can be gated into the meridians to help open blocked life-energy flow.

The acupuncture needles used in traditional acupuncture are very fine, requiring accurate location and depth insertion to produce effective results, and to not accidentally insert the needles into a nerve, a blood vessel, or a wrong point, causing pain, bleeding, and/or undesirable results. These risks make the practice of traditional acupuncture difficult to master, and patients reluctant to visit an acupuncturist. Recently, acupuncture practitioners have turned to the use of electrical energy instead of needles. The use of electrical energy has the advantage of being non-invasive. This is particularly advantageous for those individuals who are concerned about the use of needles in the procedure.

SUMMARY OF THE INVENTION

In accordance with the present invention, the method is carried out using a device capable of generating and transmitting pulsed electrical energy. Suitable devices include the Pointer Plus Excel II, the Pointer Plus, and the Pointer Plus SP4, all available from Med Servi-Systems of Canada. Other devices include the GSR 120 manufactured by Biophysica Research of Oakville, Ontario, Canada, the Medipoint Electro-acupuncture unit, manufactured by Good Health Naturally of the United Kingdom and the Healthpoint Electro-acupuncture unit, manufactured by Good Health Naturally of the United Kingdom. These devices are capable of transmitting cyclical electrical energy in the preferred form of a positive square wave spike of 4.5 volts followed by a negative wave spike of 4.5 volts directly onto various acupuncture points on the body to stimulate and clear any blockages in energy. As used herein frequency refers to one complete cycle of a positive electrical polarity followed by negative electrical polarity. The frequency of the electrical energy could be, for example, in the range of 1 to 200 hertz.

To practice the method, the patient is exposed to the allergenic substance in containers such as glass vials. The allergenic substances used will depend on the particular allergy of the patient and may include foods such as nuts, seeds, milk products, wheat products, pollen, pet dander, dust, mold or chemicals, as well as many other potential allergens. The containers containing the allergens are preferably closed and placed on the abdomen of the patient, or on the witness plate of the GSR-120 BIE Unit at the start of the procedure. The probe and grounding bar of the electrical stimulation device are touched together and the probe sensitivity is set to the desired sensitivity, preferably to the level 10. The polarity of the device should be set to bipolar and the frequency modulation should be turned on. The electrical stimulus device is set to the desired amperage and frequency. Preferably, the amperage is 0.5 micro amps and the frequency is around 10 Hz. During the procedure, it is desirable to have the patient hold a grounding bar to ensure that the electrical current passes through the patient. The electrical stimulus is applied to acupuncture meridian points at the same time that vials containing the allergens are in contact with the patient's body, or on the witness plate of the GSR-120 BIE Unit. The transmission of the electrical energy into the body through the meridian points clears blockages in the flow of life-energy. The electrical signal acts as a carrier for the natural frequency of the allergen. Thus, as the blockages are being cleared, simultaneously the cells are being exposed to the natural frequency of the allergen, carried by the electrical signal, therefore reprogramming the cell to accept the natural frequency of the allergen.

In one preferred method, the following steps are performed. The vials containing an allergen are placed near or on the patient's skin, preferably in the area of the abdomen. The device is set to the desired settings such as, for example, 4.5 volts, 0.5 micro amps and 10 Hz. Preferably, the device is first applied to the patient's first meridian point BL1 (near the eye). If using the Pointer Plus Excel II, or the Healthpoint/ Medipoint, the meridian point's exact location is pinpointed when the device emits a high pitched tone. The electrical stimulus should be applied for at least twenty seconds at each meridian point. Next, the process is repeated for the opposite BL1 point. The stimulus is then applied to the LI20 point (upper lip at side of nose) on both sides of the face. Next, the stimulus is applied for twenty seconds to each of the following pairs of points: SP1 points (big toe), ST45 points (2nd toe), BL67 points (little toe), KI1 points (plantar) KI27 points (chest) and SP21 points (midway between armpit and elbow on side of ribcage).

EXAMPLE 1

The procedure was performed on a male patient aged 34, from the town of Simcoe, Ontario, Canada. The patient was suffering from an allergy to wheat and baker's yeast. The patient was treated by the method of electrical stimulation of the meridian points according to the invention. His meridian points were stimulated with electrical energy of 0.5 micro amperes at a frequency of 10 Hz. His symptoms of allergy to wheat and baker's yeast were completely eliminated.

EXAMPLE 2

The procedure was also performed on a female patient aged 49, from the town of Oshawa, Ontario, Canada. The patient was suffering from an allergy to gluten. The patient was treated by the method of electrical stimulation of the meridian points according to the invention. Her meridian points were stimulated with electrical energy of 0.5 amperes at a frequency of 10 Hz. Her symptoms of allergy to gluten were completely eliminated.

DESCRIPTION OF THE PREFERRED EMBODIMENT

Figure 1:
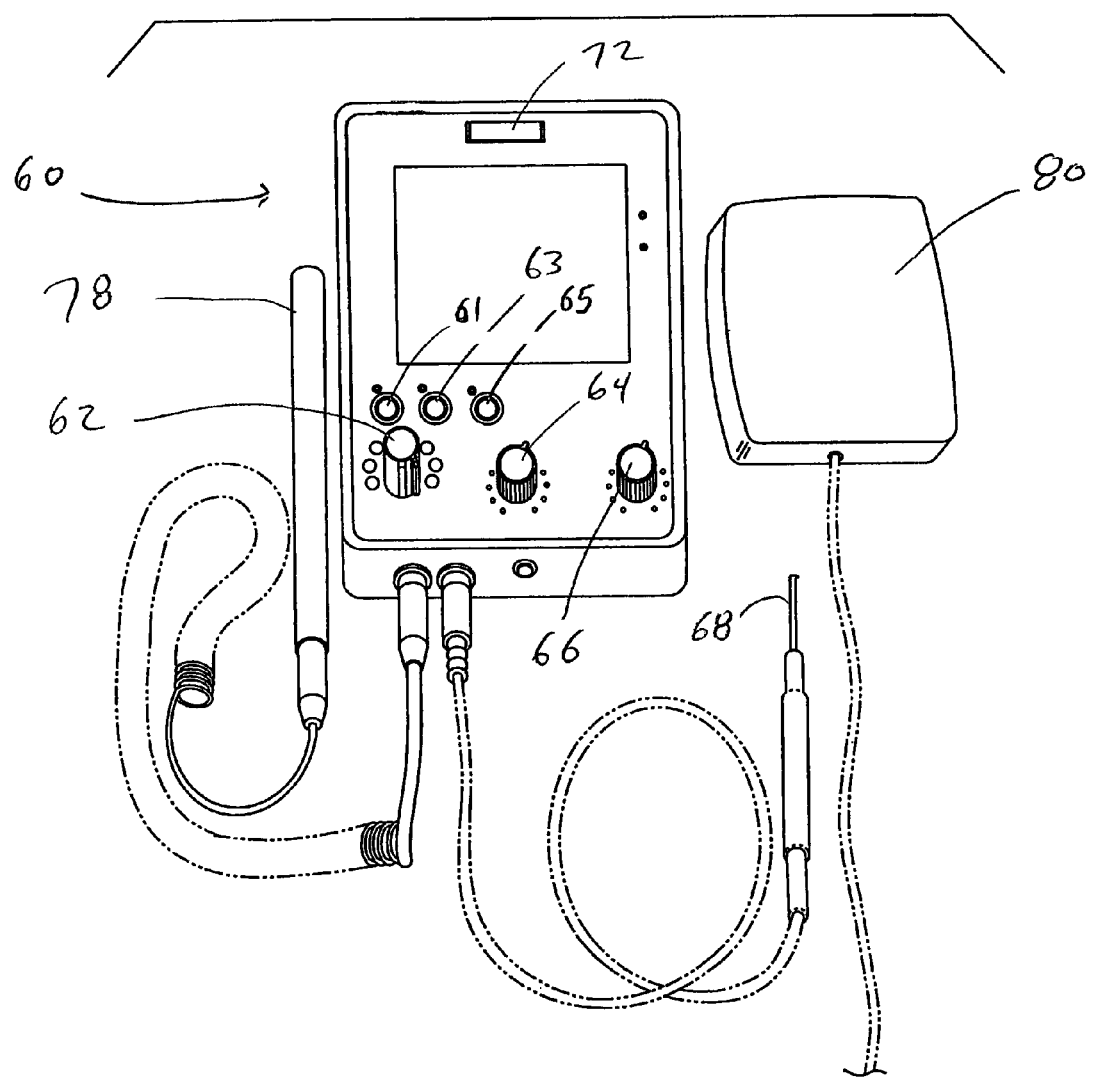
FIG. 1 is a top plan view of a device used in connection with the present invention.
Figure 12:
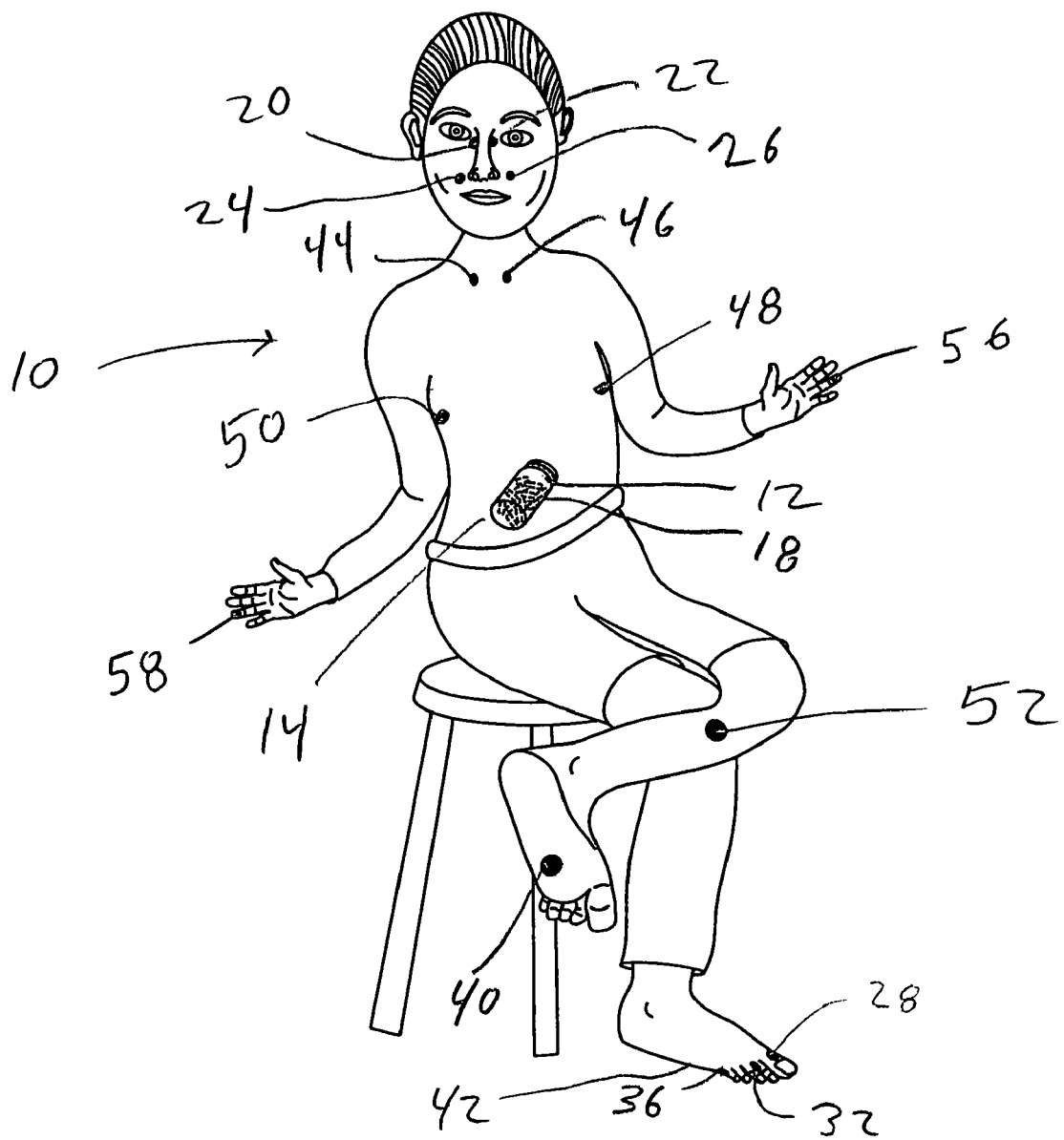
FIG. 12 is an illustration of a patient showing meridian points.

FIGS. 1-12 illustrate the method of the present invention. As shown in FIG. 1, the procedure is performed using a device 60 capable of generating and transmitting pulsed electrical energy of, preferably, 4.5 volts, 0.5 micro amps and cycled at 10 Hz, although other combinations will also work. The method is carried out using the device 60, which generates and transmits low frequency, low voltage, and low amperage electrical energy directly onto various acupuncture points on the body to stimulate and clear any blockages in life-energy. The device 60 includes controls 62, 64 and 66 to set the frequency, micro current intensity and probe sensitivity, respectively. The device 60 includes a base frequency toggle switch 61, which allows the device to be set at 100 Hz or 200 Hz. Preferably, the device is set to 100 Hz. The device 60 also includes a frequency modulation toggle switch 63 which with on and off positions. The frequency modulation toggle switch 63 should be set to "on". The device 60 also has a unipolar/bipolar toggle switch 65 which should be set to the bipolar setting. The device 60 also includes a display screen 72 for providing information about the settings of the device 60. The operator (not shown) selects the desired settings for sub-frequency, micro current intensity, and probe sensitivity using the controls 62, 64 and 66, respectively. For example, the amperage may be set to 2 micro amps and the sub-frequency may be set to 10 Hz. The device 60 has a probe 68 which emits the electrical signal. The patient 10 holds a grounding bar 78 to ensure that the electrical current passes through the patient 10 (FIG. 12). A foot petal 80 is depressed to start the generation of electrical energy. When the petal 80 is released, the electrical energy is no longer generated.

Figure 2:
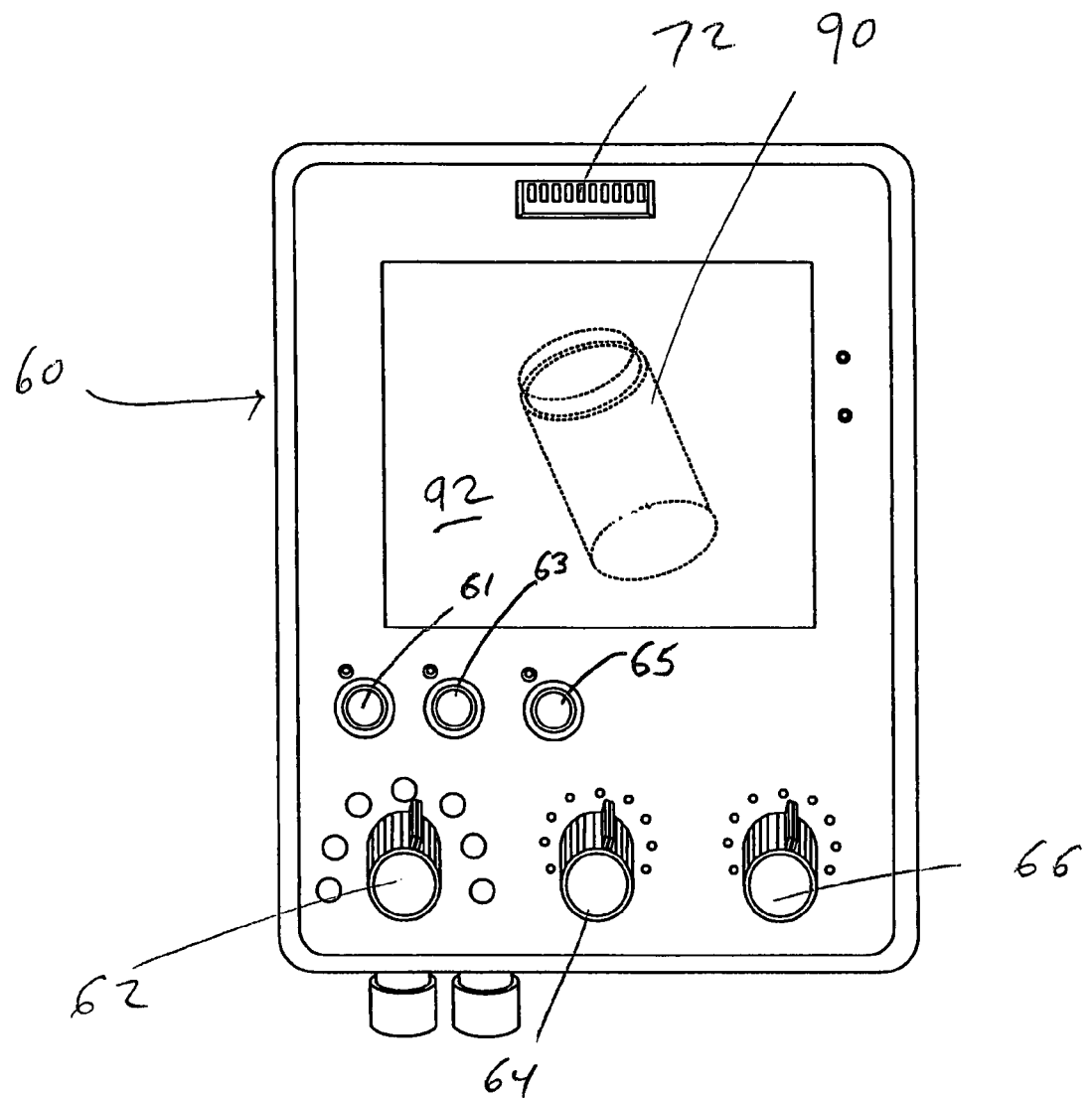
FIG. 2 is a top plan view of the device of FIG. 1 showing an allergen in the device.

In a second embodiment, as shown in FIG. 2, an allergen 90 is placed on a witness plate 92 of the device 60. The witness plate 92 is an aluminum plate on which the allergen 90 is placed.

Figure 3:
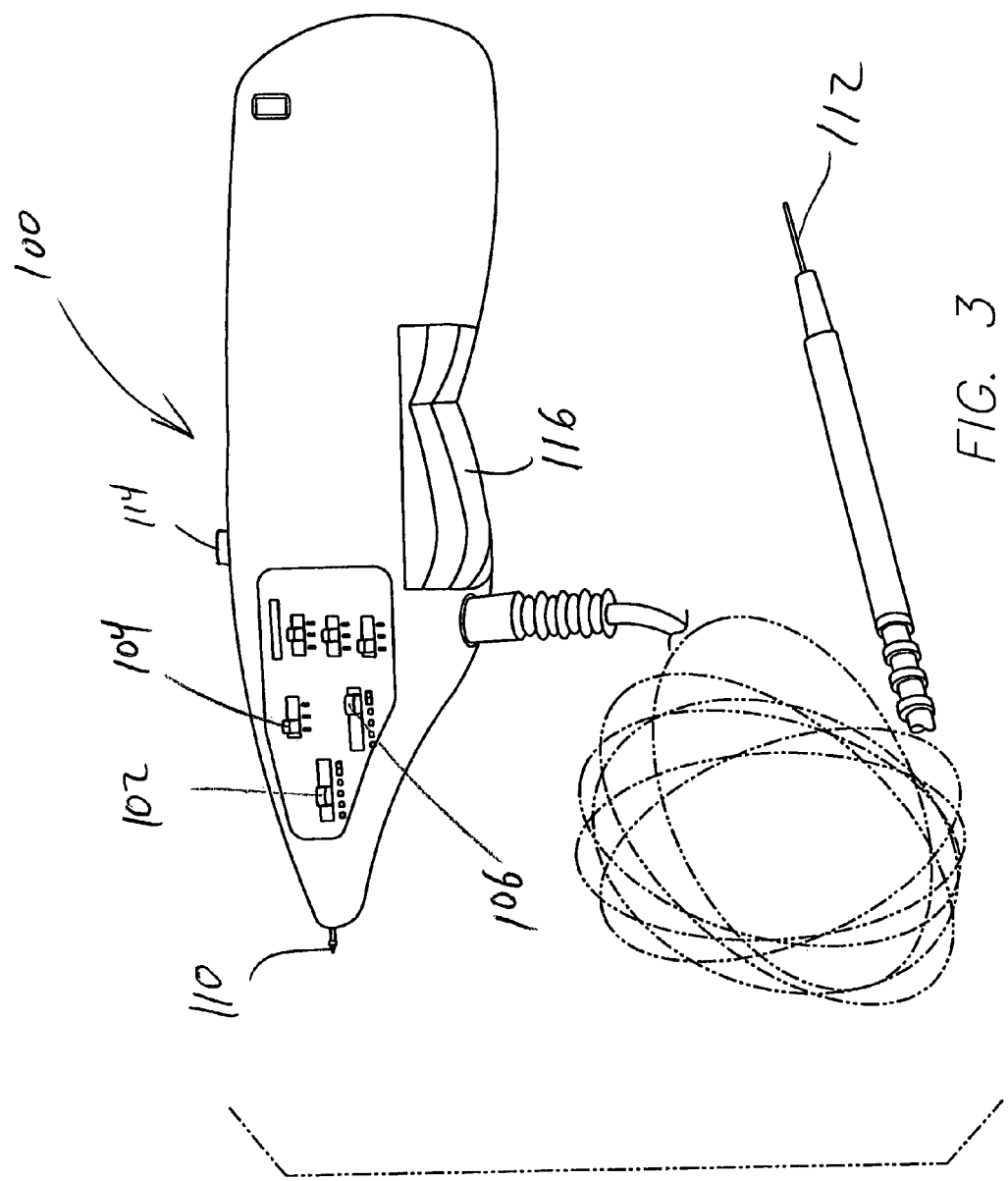
FIG. 3 is a front elevation view of a second device used in connection with the present invention.

In a third embodiment, a handheld device 100 is used, as shown in FIG. 3. The operation of the handheld device 100 is similar to that of the device 60. The controls 102, 104 and 106 set the frequency, probe sensitivity and micro current intensity, respectively. The device 100 contains a probe 110 and an extension probe 112. The device 100 also includes an on/off button 114 to start and stop the generation of electrical energy. The device 100 also includes a ground plate 116 to ground the device 100.

Figures 4, 5, 6:
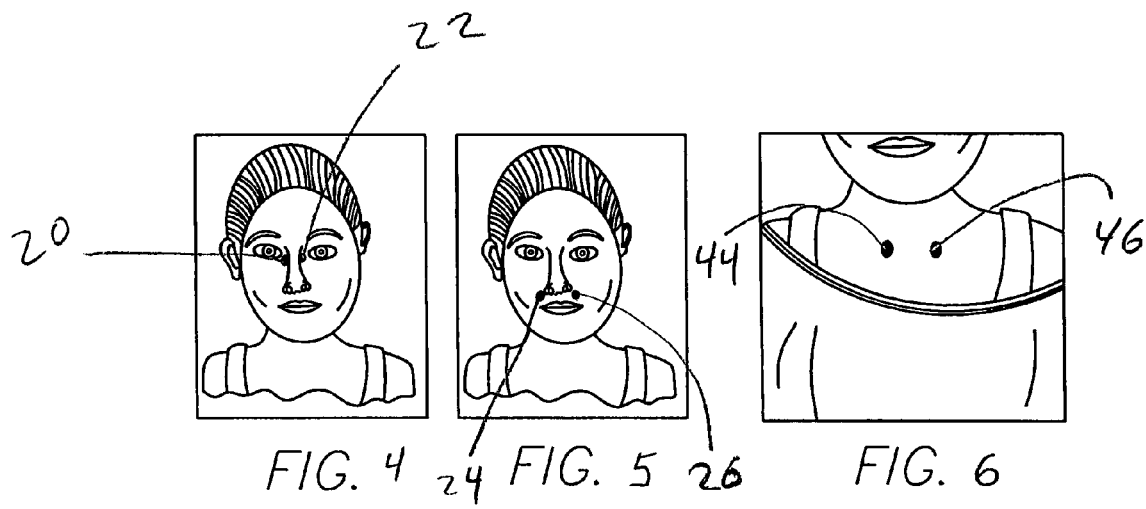
FIG. 4 is an illustration of a face of a patient showing two meridian points.
FIG. 5 is an illustration of a face of a patient showing two meridian points.
FIG. 6 is an illustration of a face of a patient showing two meridian points.
Figures 7, 8, 9:
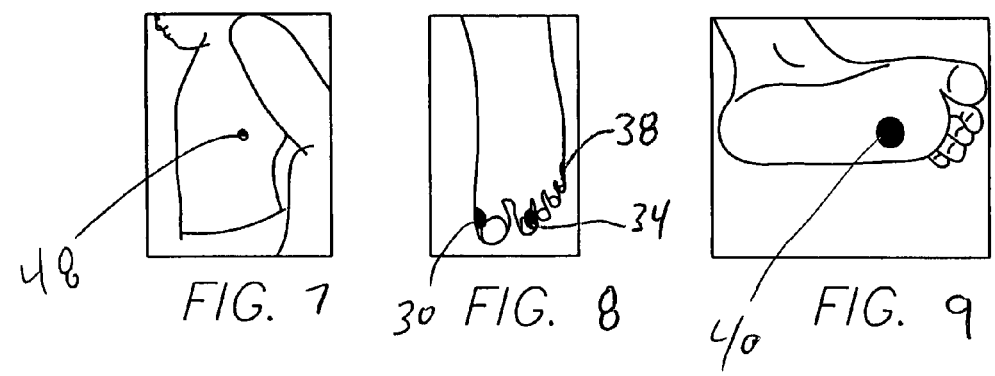
FIG. 7 is an illustration of a side of a patient showing a meridian point.
FIG. 8 is an illustration of a foot of a patient showing three meridian points.
FIG. 9 is an illustration of a foot of a patient showing a meridian point.
Figures 10, 11:
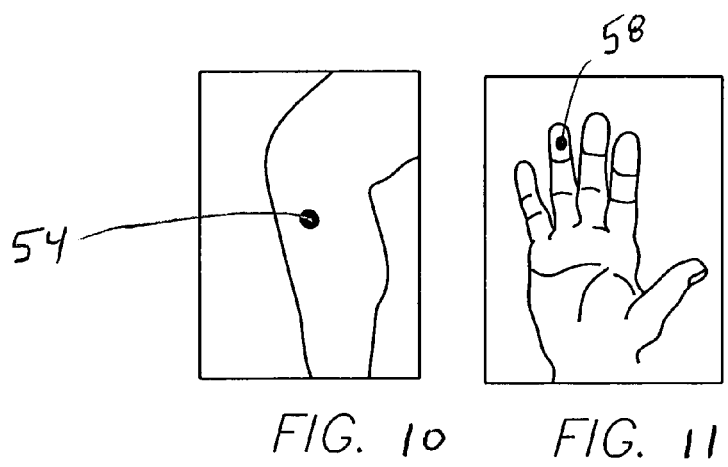
FIG. 10 is an illustration of a leg of a patient showing a meridian point.
FIG. 11 is an illustration of a hand of a patient showing a meridian point.

The electrical stimulus is applied to acupuncture meridian points on the patient 10. The transmission of the electrical energy into the body through the meridian points clears blockages in the flow of life energy. As the blockages are being cleared, simultaneously the cells are being exposed to the natural frequency of the allergens in a vial 12, placed, preferably, on the abdomen 14 of the patient; the vial contains an allergen 18 having a natural frequency. The natural frequency of the allergen 18 is picked up by the electrical signal acting as a carrier for the natural frequency of the allergen 18 and reprogramming the cell to accept this frequency The electrical stimulus may be applied to various acupuncture meridian points selected by the practitioner. In one preferred method, the following steps are performed. While the patient is holding the grounding bar 78, the probe 68 of the device 60 is first applied to the patient's BL1 meridian point 20 (FIG. 4). The BL1 meridian point's exact location is pinpointed when the device 60 emits a high pitched tone. The electrical stimulus should be applied for at least twenty seconds at this point 20. Next, the process is repeated for the opposite BL1 meridian point 22. The stimulus, through the probe 68, is then applied to the L120 meridian point 24 (FIG. 5, upper lip at side of nose) and the opposite L120 meridian point 26. Next, the stimulus, through the probe 68, is applied for twenty seconds to each of the following points: left and right SP1 meridian points 28 and 30 (FIGS. 8 and 12, big toe), left and right ST45 meridian points 32 and 34 points (FIGS. 8 and 12, 2nd toe), left and right BL67 meridian points 36 and 38 (FIGS. 8 and 12, little toe), left and right KI1 meridian points 40 and 42 (FIGS. 9 and 12, plantar), left and right KI27 meridian points 44 and 46 (FIG. 6, chest) and left and right SP2 meridian points 48 and 50 (FIGS. 7 and 12, midway between armpit and elbow on side of ribcage). To complete the process, the stimulus, through probe 68 can also be applied to the left and right SP9 meridian points 52 and 54 (FIGS. 10 and 12) and the left and right triple warmer points 56 and 58 (FIGS. 11 and 12).

It will be understood by those of skill in the art that it is possible to make variations in electrical current, voltage and frequency as well as variations in the selection of meridian points and still achieve the same results.

What is claimed is:

1. A method of reducing the symptoms of an allergic reaction of a patient to a substance comprising the steps of:
   placing the substance in a container;
   placing the container on the body of the patient;
   touching an electrical probe to a first point on the body of the patient;

generating an biphasic alternating polarity electrical current of 0.5 micro amps, with a voltage which alternates between −4.5 volts and 4.5 volts and a frequency of 10 cycles per second;

transmitting the biphasic alternating polarity electrical current from the probe to a first point on the body of the patient for a duration of 20 seconds wherein transmission of the electrical current to the patient includes an equal amount of time at −4.5 volts and 4.5 volts;

touching the electrical probe to a second point on the body of the patient; and transmitting the biphasic alternating polarity electrical current from the probe to a second point on the body of the patient.

2. The method of claim 1 wherein the container is closed.

3. The method of claim 2 wherein the container is placed on the abdomen of the patient.

4. The method of claim 1 wherein the probe is touched to acupuncture meridian points selected from the group of BL1, L120, SP1, ST45, BL67, KI1, KI27, and SP21.

5. The method of claim 1 wherein the substance is selected from the group of foods, molds, pollens, animal dander, dusts and dust mites and chemicals.

6. The method of claim 1 wherein the substance is a food product.

7. The method of claim 1 wherein the substance is animal dander.

8. The method of claim 1 wherein the substance is pollen.

9. A method of reducing the symptoms of an allergic reaction of a patient to a substance comprising the steps of:

placing the substance on a device capable of generating a biphasic alternating polarity electrical current;

touching an electrical probe in electrical communication with the device to a first point on the body of the patient;

generating a biphasic alternating polarity electrical current of 0.5 micro amps, with a voltage which alternates between −4.5 volts and 4.5 volts and a frequency of 10 cycles per second;

transmitting the electrical current from the device to the body of the patient for a duration of 20 seconds wherein transmission of the electrical current to the patient includes an equal amount of time at −4.5 volts and 4.5 volts;

touching the electrical probe to a second point on the body of the patient;

transmitting the electrical current from the device to the second point on the body.

10. The method of claim 9 wherein the probe is touched to acupuncture meridian points selected from the group of BL1, L120, SP1, ST45, BL67, KI1, KI27, and SP21.

11. The method of claim 9 wherein the substance is selected from the group of foods, molds, pollens, animal dander, dusts and dust mites and chemicals.

12. The method of claim 9 wherein the substance is a food product.

13. The method of claim 9 wherein the substance is animal dander.

14. The method of claim 9 wherein the substance is pollen.

* * * * *